United States Patent [19]

England

[11] 4,097,081
[45] Jun. 27, 1978

[54] DEVICE FOR INSERTING AND REMOVING CONTACT LENSES

[76] Inventor: Robert C. England, 6710 C.R. 191, Bellevue, Ohio 44811

[21] Appl. No.: 815,679

[22] Filed: Jul. 14, 1977

[51] Int. Cl.² ............................................. A61F 9/00
[52] U.S. Cl. ............................. 294/1 CA; 294/64 R
[58] Field of Search ........................ 294/1 CA, 64 R; 128/303 R; 206/5.1; 351/160

[56] References Cited

U.S. PATENT DOCUMENTS

| | | | |
|---|---|---|---|
| 2,384,334 | 9/1945 | Olson | 294/64 R |
| 3,091,328 | 5/1963 | Leonardos | 294/1 CA UX |
| 3,129,971 | 4/1964 | Kobler | 294/1 CA X |
| 3,647,380 | 3/1972 | Middleton | 294/64 R X |
| 3,791,689 | 2/1974 | Boone et al. | 294/1 CA |
| 3,934,914 | 1/1976 | Carruthers | 294/1 CA |

FOREIGN PATENT DOCUMENTS 2,301,538  7/1974  Germany ........................ 294/1 CA

*Primary Examiner*—Johnny D. Cherry
*Attorney, Agent, or Firm*—John Harrow Leonard

[57] ABSTRACT

An elongated resilient cylindrical body of small diameter has at its forward end a contact lens holding suction cup. A small diameter axial duct extends entirely through the body. The duct is open at its forward end at the central portion of the cup and at its opposite end at the distal end of the body. The body has a tapered portion which is of progressively decreasing diameter from a location near the distal end of the body to the distal end. The distal end of the body thus presents rearwardly a relatively small annular contact sealing area surrounding the rear end of the duct. The tapered portion is related to the diameters of the body and duct, and to the resilience of the body, so that, with the body held between the thumb and one finger of the user's hand, the tapered portion can be squeezed lightly radially therebetween, while another finger of the hand covers and closes the rear end of the duct, thereby compressing the tapered portion to a degree sufficient to reduce the volumetric capacity of the duct and thereby retain to a greater degree the holding force of the cup.

7 Claims, 7 Drawing Figures

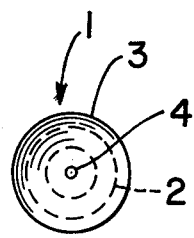
FIG. 2
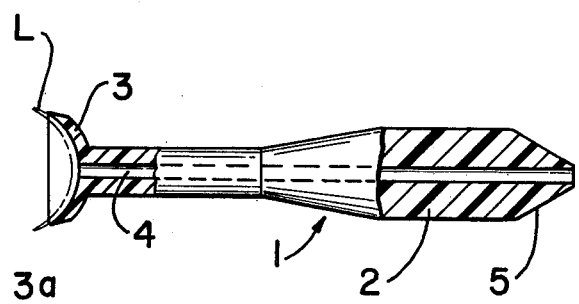
FIG. 1
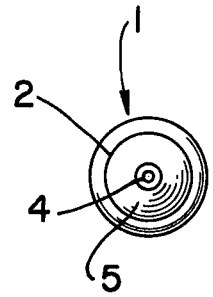
FIG. 3
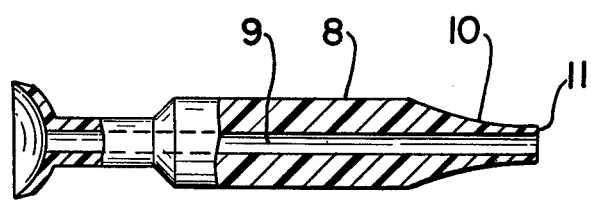
FIG. 4
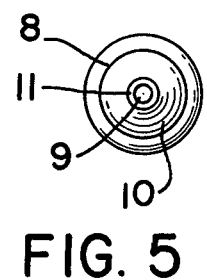
FIG. 5
FIG. 6
FIG. 7
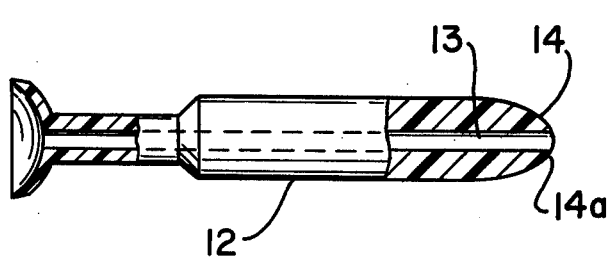
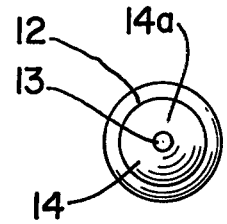

DEVICE FOR INSERTING AND REMOVING CONTACT LENSES

BACKGROUND OF THE INVENTION (1) Field of Invention

Suction cup device for inserting, holding, and removing contact lenses.

(2) Prior Art

Early devices for this purpose have been provided which include bulbs or extraneous suction creators which are meant to be operated, when the cup is in contact with the lens, to provide a relatively high degree of suction. These devices are dangerous, because of the relatively high and very large capacity of suction effective in the cup. This is dangerous because, if the cup is inadvertently placed against the eyeball, instead of the lens, while the suction is applied, the suction itself, or the pull of the cup on the eyeball should the user suddenly jerk it in a direction away from the eyeball, can damage the eye.

Subsequently, some unpatented contact lens holding devices have been available on the market and others are disclosed in prior patents.

One such subsequent prior holding device comprises a slightly resilient elongated cylindrical body with a suction cup at its forward end, and a duct leading from the central portion of the cup endwise of the body wherein it connects with one end of a metal tube disposed axially within the body. At a location remote from the suction cup, the tube is bent to extend outwardly, radially of the body, so that its rear end is open through the side wall of the body in a position such that it can be closed by the application of the thumb or finger of the user's hand to the open end of the tube while the body is held between the thumb and finger.

Another subsequent holding device for a like purpose dispenses with the metal tube. Instead, an axial duct is provided in the body and extends axially from the central portion of the cup, or forward end of the body, entirely through the body. The duct is open at both ends. In this prior device, the distal end of the body is concave so that one finger of the user's hand could be pressed into the concavity and close the distal end of the duct while the body is gripped between the thumb and another finger. The latter structure is disclosed in a German patent to Norbert A. Gunther, U.S. Pat. No. 2,301,538, of July 18, 1974.

These subsequent devices eliminate the specific disadvantages of the high degree and large capacity of suction produced by extraneous suction creators, in that only such limited suction can be created by the cup itself that it can be relieved quickly in case the patient should inadvertently place the remover directly against the eyeball, and, in panic, jerk it away. It is only necessary that the user let go of the holding device whereupon it can immediately fall free. However, these latter forms have a disadvantage in that the suction creating capacity of the cup is very limited, and part of the suction is dissipated due to the air capacity of the duct. Accordingly, there is danger of the suction being reduced to such a degree as to cause accidental release of the lens by the cup.

As to the German patent device, it is somewhat awkward to use because of the necessity of holding the device between the thumb and finger and seating another finger in the concavity at the distal end to close the duct.

In all of these devices of the non-bulb type which, for reducing accidental danger to the eye depend on the limited suction created by flexure and self-restoration of the cup to hold the lens, there is a tendency for the lens to be held insecurely. As mentioned, the slight distortion of the cup and resultant limited suction creating capacity which normally results from the self-restoration of the cup is reduced to a large degree because of the relatively large volume of air in the duct.

SUMMARY

The present invention is more effective in that a body of the general character described is further characterized by being contoured and made sufficiently resilient so that the portion of it which is held between the thumb and forefinger of the user's hand, can be squeezed lightly and thereby compressed readily to a degree to reduce the volumetric capacity of the duct, or even to close the duct if the end of the duct is not closed by another finger of the holding hand. Reducing the volumetric capacity of the duct retains to a greater degree the effectiveness of the initial limited suction created by the cup. This ready compressibility is best achieved by tapering of the body from a point sufficiently far from its distal end, entirely to the distal end, so that the length of the portion of the duct which can be compressed to reduce its volumetric capacity is adequate to assure retention of ample suction of the cup while at the same time exposing endwise at the distal end of the body a very small rim or annular area coaxial with the duct which can readily be closed by another finger of the holding hand and opened by very slight movement of said other finger. Further the duct can be closed by the squeezing pressure, whether the distal end is closed or not.

A great advantage is that the suction is immediately released by letting go of the device, whereupon it falls free, thus averting danger of damage to the eye by suction applied directly thereto by the cup or by pulling the device away from the eye while the cup is held by suction against the eyeball.

The present device is particularly advantageous for use by patients who are not dexterous enough to remove contact lenses with the typical open-pull-blink method.

Various other objects and advantages will become apparent from the following description wherein reference is made to the drawings.

BRIEF DESCRIPTION OF THE DRAWINGS

FIG. 1 is a longitudinal view, partly in section, of a contact lens holding device embodying the principles of the present invention;

FIG. 2 is a left end elevation of the device illustrated in FIG. 1;

FIG. 3 is a right end elevation of the device illustrated in FIG. 1;

FIG. 4 is a fragmentary longitudinal sectional view of a contact lens holding device illustrating a modification of of the taper of the distal end;

FIG. 5 is a right end elevation of the device of FIG. 4;

FIG. 6 is a view similar to FIG. 4 showing another modification of the taper of the distal end; and FIG. 7 is a right end elevation of the device of FIG. 6.

Referring to FIG. 1, the contact lens holding device, indicated generally at 1, comprises an elongated cylindrical body 2, of resilient material. The body has at its forward end a suction cup 3 with a concave surface exposed forwardly of the body for engaging a contact lens L. The cup 3 has a soft, flexible rim 3a and is, itself, readily distortable by forward endwise pressure so as to flex and conform to the adjacent convex face of the lens. It is self-restoring so as to create a suction for holding the lens.

The body 2 has an axial duct 4 of small diameter which, at the forward end of the body, is connected with the interior of the cup near, and preferably at, its central portion. The duct extends axially of the body, entirely therethrough, to the distal end of the body. The body has a rear portion 5 which is of progressively reduced diameter beginning at a location spaced from the distal end of the body and continuing entirely to the distal end. The taper is such relative to the normal diameter of the body 2, and also to the diameter of the duct 4, that it presents a very small annular seating surface or rim at the distal end of the body surrounding and coaxial with the rear end of the duct 4. As a result of this small area, the end of the duct can readily be covered by a finger of the hand of the user while the body is held between the thumb and another finger, and can be uncovered by slight movement of the closing finger.

Thus the holding device can be applied readily to the lens by pressing the body endwise lightly so as to engage the cup 3 with the convex face of the lens L and cause it to flex and conform substantially thereto, and then closing the rear end of the duct 4 so that a vacuum is developed by the cup for holding the lens L for installing the lens on the eyeball, or removing it therefrom, as the case may be. The vacuum is eliminated by uncovering the distal end of the duct 4, thus releasing the cup 3 from the lens L. Due to the small area of annular rim around the rear end of the duct 4, this release can be effected by a very slight movement of the duct closing finger.

Here it is to be noted that the duct must be of substantial size for efficiency in manufacture, and also to reduce clogging or obstruction by foreign matter. In view of the limited amount of air that can be expelled by pressing the cup into contact with the face of the lens L, the size of the duct can affect greatly the degree and amount of suction created by the cup. In effect, the larger the volumetric capacity of the duct, the greater is the reduction in what would otherwise be the full suction that can be created by the cup.

In order to maintain the suction of the cup near the normal maximum capacity which it would have were there no duct, the tapered portion 5 of the body is such in relation to the external diameter of the body 1 and the diameter of the duct 4 that it permits compression of the tapered portion of the body radially, by very light force applied radially by the thumb and finger, to a degree to close, or greatly decrease the volumetric capacity of, a portion of the duct 4 between its distal end and the cup. This reduces the amount of air which otherwise would be entrapped in the duct and be slightly compressed therein upon applying the cup to the lens and which would partially reduce, or partially relieve, the vacuum created by the cup. At the same time the device is such that a release of the collapsing pressure and opening of the distal end or, in short, the mere release of the body by the fingers and thumb, eliminates completely the vacuum, so that the device is instantly freed from the lens, or the eye if the cup happens to be placed against the eye.

With this combination of features, the vacuum is small enough to reduce to a miniscular amount the danger to the eye, yet is great enough to hold the lens effectively.

As illustrative of preferred proportions of the form of the device illustrated in FIG. 1, the radius of the cup may be within a range of 6 to 10 mm., with 7 mm. the usual preferred size. However, one may depart from this range in extreme cases.

The length of the body 2 may be that illustrated, or somewhat longer, so that it is within a range such that the fingers are not too far removed from the eye when the cup 3 is in position against the lens mounted on the eyeball. Also, undue length of the body unnecessarily increases the volumetric capacity of the duct 4, and thus reduces the effective solution that can be developed or created by the cup 3.

Generally the concave face of the cup is wetted before application to the lens for better adhesion.

In the form illustrated in FIGS. 1 through 3, the tapered portion 5 is preferably frusto-conical with its side wall linear in the longitudinal section.

On the other hand, it may be that the greater compressibility and reduction of the volumetric capacity of the duct may be desired in which case the distal end of the body may have the form illustrated in FIGS. 4 and 5. As therein shown, the body 8, corresponding to the body 2, has a duct 9, and, near its distal end, a tapered portion 10 which is of circular cross section and of progressively less diameter from a location spaced from the distal end entirely to the distal end. In this portion 10, the taper is such that the distal end is approximately a point, its external diameter being very slightly greater than the internal diameter of the duct 9 so that the annular seating area surrounding the distal end of the duct, indicated at 11, is practically a line defining a circle. This is best accomplished by making the peripheral wall of the portion 10 curvilinear and concave in the longitudinal section of the body. The longer the tapered end portion of the body, the greater is the degree to which the radial compression can be effected readily and the volumetric capacity of the duct reduced.

In FIGS. 6 and 7, there is illustrated a similar body 12 corresponding to the body 2, having a duct 13, in which the distal end 14 of the body is progressively tapered from a location spaced therefrom entirely to the distal end, but with the peripheral wall 14a of the distal end curvilinear and convex radially outwardly in the longitudinal section of the body.

Thus, with the present device, greater effectiveness of the holding of the lens by the cup is obtained with the least awkward, and most normal, flexure of the fingers and thumb, while at the same time the suction is maintained within a safe limit yet can be released completely readily by releasing the fingers and thumb from the device, or by relieving the pressure on the tapered portion and uncovering the duct at the distal end of the body.

Having thus described my invention, I claim:

1. A device for inserting and removing contact lenses comprising:
    an elongated cylindrical body of resilient material having a forward end and a distal end;
    a resilient suction cup coaxial with, and carried by, the body at said forward end and having a concave face facing forwardly of the body;
    said body having a through axial duct of small diameter relative to the diameter of the cup, and connected at its forward end with the central portion of said cup and opening at its rear end through the rearmost portion of the distal end of the body;

characterized in that:

said body has a coaxial tapered portion tapering from a location spaced from the distal end to the distal end;

said duct is coaxial with said tapered portion;

said rearmost portion of the distal end of the body is in the form of a relatively small annular contact area surrounding the rear open end of the duct and which can be engaged by one finger of the hand of a user to seal the distal end of the duct while the body is held between the thumb and another finger of said hand;

the taper of said tapered portion, relative to the diameter of the duct, being such that the tapered portion can be compressed to a degree to reduce materially the size and volumetric capacity of the duct, thereby to render more effective the suction created by flexure and self-restoration of the cup resulting from the cup first being pressed against the lens in a direction toward the eye and moved in the opposite direction for withdrawing the lens from the eye by squeezing the tapered portion lightly radially between the thumb and said other finger of the user's hand and holding the tapered portion in squeezed condition while the body is held between said thumb and said other finger and the duct sealed at least near to its distal end.

2. The device according to claim 1 wherein said tapered portion is sufficiently self-restoring so that the suction created by the cup can be augmented by releasing the squeezing force of the thumb and said other finger while the cup is applied to the lens with said distal end of the duct closed by said one finger.

3. The device according to claim 1 wherein said relation of the tapered portion and the diameter of said duct is such that at least part of said tapered portion to be squeezed between said thumb and said other finger is such that light squeezing pressure so applied can completely collapse and close the part of the duct therein.

4. The device according to claim 3 wherein the distal end of the body is only slightly larger in external diameter than the internal diameter of the duct.

5. The device according to claim 1 wherein said tapered portion is essentially frusto-conical, with its smaller end at the distal end of the body.

6. The device according to claim 1 wherein said tapered portion is of circular cross section throughout at least most of its length, and its peripheral wall is curvilinear and concave in longitudinal section.

7. The device according to claim 1 wherein the peripheral wall of the tapered portion is curvilinear and convex in longitudinal section.

* * * * *